United States Patent [19]

Morinaka et al.

[11] 4,128,646
[45] Dec. 5, 1978

[54] PYRIMIDO[5,6-B]QUINOXALINE-4-(3H)-ONE-2-CARBOXYLIC ACID COMPOUNDS

[75] Inventors: Yasuhiro Morinaka; Kazuo Takahashi, both of Amimachi, Japan

[73] Assignee: Mitsubishi Yuka Pharmaceutical Co., Ltd., Tokyo, Japan

[21] Appl. No.: 865,135

[22] Filed: Dec. 28, 1977

[30] Foreign Application Priority Data

Dec. 28, 1976 [JP] Japan .................................. 51-158332
Nov. 30, 1977 [JP] Japan .................................. 51-143458

[51] Int. Cl.² .................... A61K 31/505; C07D 487/04
[52] U.S. Cl. ...................................... 424/251; 544/251
[58] Field of Search ....................... 260/251.5; 424/251

[56] References Cited

U.S. PATENT DOCUMENTS

| | | | |
|---|---|---|---|
| 2,993,898 | 7/1961 | Petering | 260/251.5 |
| 3,048,578 | 8/1962 | Erlenmeyer et al. | 260/251.5 |
| 4,011,324 | 3/1977 | Althuis | 424/251 |

*Primary Examiner*—Paul M. Coughlan, Jr.
*Attorney, Agent, or Firm*—Oblon, Fisher, Spivak, McClelland & Maier

[57] ABSTRACT

Substituted pyrimido[5,6-b]quinoxaline-4(3H)-one-2-carboxylic acid compounds each represented by the formula

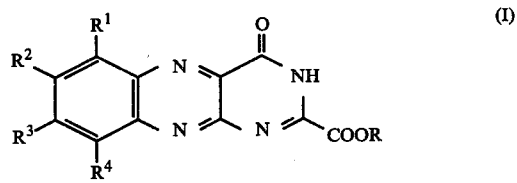

wherein: R designates a member selected from the group consisting of hydrogen, alkyl groups having 1 to 4 carbon atoms, benzyl group, and phenyl group; and each of $R^1$, $R^2$, $R^3$, and $R^4$ independently designates a member selected from the group consisting of hydrogen, alkyl group having 1 to 4 carbon atoms, alkoxy groups having 1 to 4 carbon atoms, halogens, benzyloxy group, hydroxyl group, alkylthio groups having 1 to 4 carbon atoms, and alkylenedioxy groups having 1 to 4 carbon atoms and formed by the bonding of two of $R^1$, $R^2$, $R^3$, and $R^4$, or pharmacologically acceptable salts of said compounds.

4 Claims, No Drawings

PYRIMIDO[5,6-B]QUINOXALINE-4-(3H)-ONE-2-CARBOXYLIC ACID COMPOUNDS

BACKGROUND OF THE INVENTION

This invention relates generally to pyrimidoquinoxaline derivatives and a process for producing the same and, further, to a remedy comprising the same for treatment of allergic asthma.

It is reported by Cox, et al, (Adv. in Drug Res. 5, 115 (1970) ) that sodium chromoglycate, which has been developed in recent years, is effective for treatment of allergic bronchial asthma. This compound is thought to exhibit its effectiveness by inhibiting the discharge of a chemical mediator from most cells which are formed as a result of an antigen antibody reaction caused by a reagin antibody. However, a disadvantageous feature of this compound is that it cannot be absorbed by oral administration, and at present it is being used as a powder inhalant.

Needless to say, an allergic asthma remedy which can also be orally administered would be highly effective.

SUMMARY OF THE INVENTION

The results of our research indicate that a specific kind of new pyrimidoquinoxaline derivatives has an anti-allergic action equivalent to that of sodium chromoglycate in animal experiments and, moreover, exhibits a powerful effectiveness when orally administered which is comparable to that it exhibits when intravenously injected. This suggests that this compound will be useful as a preventive medicine for allergic asthma.

Accordingly, it is an object of this invention to provide an allergic asthma remedy which can also be orally administered.

Another object of the invention is to provide new pyrimidoquinoxaline derivatives.

Still another object of the invention is to provide a process for producing these pyrimidoquinoxaline derivatives.

According to this invention these and other objects thereof have been achieved by providing and utilizing substituded pyrimido [5,6-b] quinoxaline-4(3H)-one-2-carboxylic acid compounds each represented by the formula (I) set forth hereinafter or pharmacologically acceptable salts thereof.

DETAILED DESCRIPTION

1. Pyrimidoquinoxaline derivatives

The pyrimidoquinoxaline compounds provided by this invention are substituted pyrimido [5,6-b] quinoxaline-4(3H)-one-2-carboxylic acids each represented by the following formula (I), esters thereof, and pharmacologically acceptable salts thereof.

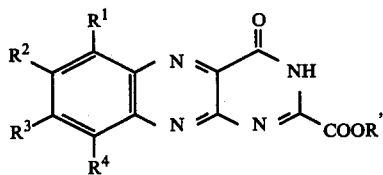

wherein: R represents hydrogen or an alkyl group having 1 to 4 carbon atoms, benzyl group, or a phenyl group; each of $R^1$, $R^2$, $R^3$, and $R^4$ independently represents hydrogen, an alkyl group having 1 to 4 carbon atoms, an alkoxy group having 1 to 4 carbon atoms, a halogen, benzyloxy group, hydroxyl group, an alkylthio group having 1 to 4 carbon atoms, or an alkylenedioxy group having 1 to 4 carbon atoms and formed by the bonding of two of $R^1$, $R^2$, $R^3$ and $R^4$.

According to this invention, for the substituents $R^1$, $R^2$, $R^3$, and $R^4$, the specific substituents named above are considered, but it is possible to synthesize the pyrimidoquinoxaline derivatives having the other substituents and these should have considerable medicinal effectiveness.

For these substituents $R^1$, $R^2$, $R^3$, and $R^4$, the following may be considered in addition to hydrogen: methyl, ethyl, butyl, methoxy, isopropoxy, butoxy, chloro, bromo, benzyloxy, hydroxy, methylthio, butylthio, and others.

Specific examples of the compound (I) are as enumerated below. Here, [A] represents a substituent group as set forth above, and in the case of plurality of [A]s, they may be the same or may be different.

(1) Non-substituted product $R^1 = R^2 = R^3 = R^4 = H$ (2) Monosubstituted product
  (a) 6 - substitution $R^2 = R^3 = R^4 = H$ $R^1 = [A]$ (b) 7 - substitution $R^1 = R^3 = R^4 = H$ $R^2 = [A]$ (c) 8 - substitution $R^1 = R^2 = R^4 = H$ $R^3 = [A]$ (d) 9 - substitution $R^1 = R^2 = R^3 = H$ $R^4 = [A]$ (3) Disubstituted product
  (a) 6,9-substitution $R^2 = R^3 = H$ $R^1 = [A], R^4 = [A]$ (b) 7,8-substitution $R^1 = R^4 = H$ $R^2 = [A], R^3 = [A]$ In the case wherein the substituent groups are vicinal as in the 7,8-substitution, $R^2$ and $R^3$ may be mutually bonded and form ($R^2 - R^3$) methylenedioxy, ethylenedioxy,etc.
  (c) 6,7-substitution $R^3 = R^4 = H$ $R^1 = [A], R^2 = [A]$, or $R^1 - R^2$ = methylenedioxy or ethylenedioxy (d) 6,8-substitution $R^2 = R^4 = H$ $R^1 = [A], R^3 = [A]$ (e) 7,9-substitution $R^1 = R^3 = H$ $R^2 = [A], R^4 = [A]$ (f) 8,9-substitution $R^1 = R^2 = H$ $R^3 = [A], R^4 = [A]$, or $R^3 - R^4 =$ methylenedioxy or ethylenedioxy (4) Trisubstituted product
(a) 6,7,8-substitution $R^1 = [A], R^2 = [A], R^3 = [A]$, or $R^1 - R^2$ or $R^2 - R^3 =$ methylenedioxy or ethylenedioxy $R^4 = H$ (b) 7,8,9-substitution $R^1 = H$
$R^2 = [A], R^3 = [A], R^4 = [A]$, or $R^2 - R^3$ or $R^3 - R^4 =$ methylenedioxy or ethylenedioxy (c) 6,7,9-substitution $R^1 = [A], R^2 = [A]$, or $R^1 - R^2 =$ methylenedioxy or ethylenedioxy $R^3 = H$ $R^4 = [A]$ (d) 6,8,9 substitution $R^1 = [A]$ $R^2 = H$ $R^3 = [A], R^4 = [A]$, or $R^3 - R^4 =$ methylenedioxy or ethylenedioxy (5) Tetrasubstituted product $R^1 = [A], R^2 = [A], R^3 = [A], R^4 = [A]$, or $R^1 - R^2, R^2 - R^3$, or $R^3 - R^4 =$ methylenedioxy or ethylenedioxy Of these derivatives, those of 7-, 8-, and 7,8-substituted products, in cases, are produced from readily available starting materials and can be easily synthesized.

Specific examples of these compounds are as follows: $R^1$ through $R^4 =$ H (non-substituted), 6,9-dimethyl-, 6,9-dimethoxy-, 6,9-dichloro-, 6-methyl-, 9-methyl-, 6,9-dibutyl-, 6-butyl-, 9-butyl-, 6,9-diisopropyl-, 6-methoxy, 9-methoxy-, 6,9-dibutoxy-, 6-butoxy-, 9-butoxy-, 6,9-diisopropoxy-, 6-chloro-, 9-chloro-, 6,9-dibromo-, 6-benzyloxy-9-methoxy-, 6,9-dibenzyloxy-, 6-hydroxy-9-methoxy, 6,9-hydroxy-, 6,9-dimethylthio-, 6-methylthio, 6,9-dibutylthio-, 6-isopropylthio-, 6-butylthio-, 7,8-dimethyl-, 7,8-dimethoxy-, 7,8-dichloro-, 7-methyl-, 8-methyl-, 7,8-dibutyl-, 7-butyl, 8-butyl-, 7,8-diisopropyl-, 7-methoxy-, 8-methoxy-, 7,8-dibutoxy-, 7-butoxy-, 8-butoxy-, 7,8-diisopropoxy-, 7-chloro-, 8-chloro-, 7,8-dibromo-, 7-benzyloxy-8-methoxy-, 7,8-dibenzyloxy-, 7-hydroxy-8-methoxy, 7,8-hydroxy-, 7,8-dimethylthio-, 7-methylthio-, 7,8-dibutylthio-, 7-isopopylthio, 7-butylthio-, 7,8-methylenedioxy-, 7,8-ethylenedioxy-, 6,7-dimethyl-, 6,7-dimethoxy-, 6,7-dichloro-, 6,7-dibutyl-, 6,7-diisopropyl-, 6,7-dibutoxy-, 6,7-diisopropoxy-, 6,7-dibromo-, 6-benzyloxy-7-methoxy-, 6,7-dibenzyloxy-, 6-hydroxy-7-methoxy-, 6,7-hydroxy-, 6,7-dimethylthio-, 6,7-dibutylthio-, 6,7-methylenedioxy-, 6,7-ethylenedioxy-, 6,8-dimethyl-, 6,8-dimethoxy-, 6,8-dichloro-, 6,8-dibutyl-, 6,8-diisopropyl-, 6,8-dibutoxy, 6,8-diisopropoxy-, 6,8-dibromo, 6-benzyloxy-8-methoxy-, 6,8-dibenzyloxy, 6-hydroxy-8-methoxy-, 6,8-hydroxy-, 6,8-dimethylthio-, 6,8-dibutylthio-, 7,9-dimethyl-, 7,9-dimethoxy-, 7,9-dichloro-, 7,9-dibutyl-, 7,9-diisopropyl-, 7,9-dibutoxy-, 7,9-diisopropoxy-, 7,9-dibromo-, 7-benzyloxy-9-methoxy-, 7,9-dibenzylthio-, 7-hydroxy-9-methoxy-, 7,9-hydroxy-, 7,9-dimethylthio, 7,9-dibutylthio-, 8,9-dimethyl-, 8,9-dimethoxy-, 8,9-dichloro-, 8,9-dibutyl-, 8,9-diisopropyl-, 8,9-dibutoxy-, 8,9-dibromo-, 8-benzyloxy-9-methoxy-, 8,9-diisopropoxy-, 8,9-dibromo-, 8,9-dibenzyloxy-, 8-hydroxy-9-methoxy-, 8,9-hydroxy-, 8,9-dimethylthio-, 8-methylthio-, 8,9-dibutylthio-, 9-isopropylthio-, 9-butylthio-, 8,9-methylenedioxy-, 8,9-ethylenedioxy-, 6,7,8-trimethyl-, 6,7,8-trimethoxy-, 6,7,8-trichloro-, 6,7,8-tributyl-, 6,7,8-tributoxy-, 7,8,9-trimethyl-, 7,8,9-trimethoxy-, 7,8,9-trichloro-, 7,8,9-tributyl-, 7,8,9-tributoxy-, 6,7,9-trimethoxy-, 6,7,9-trichloro-, 6,7,9-tributyl-, 6,7,9-tributoxy-, 6,8,9-trimethyl-, 6,8,9-trimethoxy-, 6,8,9-trichloro-, 6,8,9-tributyl-, 6,8,9-tributoxy-, 6,7,8,9-tetramethyl-, 6,7,8,9-tetramethoxy-, 6,7,8,9-tetrachloro-, 6,7,8,9-tetrabutyl-, and 6,7,8,9-tetrabutoxy.

In these cases, while R may represent any of the aforedescribed groups, a specific example thereof is H (i.e., a free acid).

Specific examples of R in the case where this substituted pyrimido[5,6-b]quinoxaline-4(3H)-one-2-carboxylic acid compound is an ester are methyl, ethyl, n-propyl, isopropyl, n-butyl, benzene, and phenyl.

In the case where this carboxylic acid compound is a pharmacologically acceptable salt, typical examples of salt-forming cations include metal ions and amine ions (inclusive of ammonium). Specific examples are Na, K, Mg, Ca, Al, Cu, and the like, and ammonia, tris (hydroxymethyl) aminomethane, N, N-bis(hydroxyethyl) piperazine 2-amino-2-methyl-1-propanol, and mono-, di- and tri-ethanolamines.

Since this substituted pyrimido [5,6-b]quinoxaline-4(3H)-one-2-carboxylic acid compound has basic nitrogen at the 5-position and the 10-position, salts can be made together with acids. The salts of this case, also, are within the purview of this invention provided that they are pharmacologically acceptable. Examples of the acids in this case are hydrogen chloride, sulfuric acid, hydrogen bromide, and methanesulfonic acid.

2. Synthesis of compounds

While a compound of the formula (I) can be synthesized by any appropriate process, one preferable process comprises the following steps.

2-1. Synthesis process A

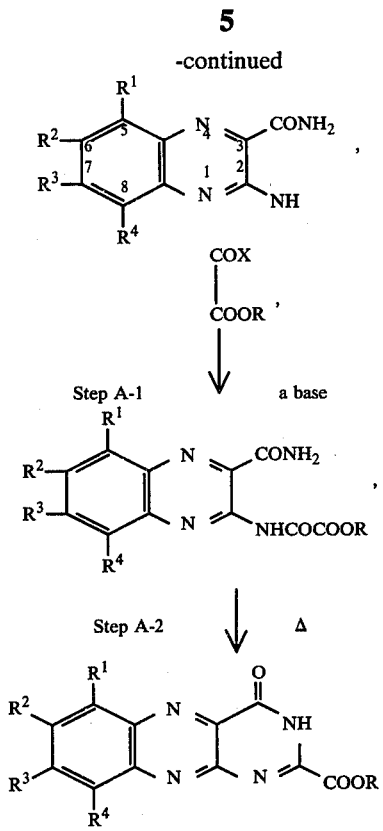

(R, R¹ through R⁴, and X have the same respective meanings as set forth hereinbefore.

By this synthesis process, the compound (IV) is obtained as an intermediate, which is caused to undergo ring closure by heating. If desirable, however, it is also possible to carry out the reaction under ring-closing conditions from the beginning thereby to obtain directly the compound (I). Nevertheless, it is more advantageous to first synthesize the intermediate compound IV under relatively mild conditions, isolate this in accordance with necessity, and then carry out the ring closure step thereof. The reason for this is that the subsequent isolation purification of the compound (I) is then extremely facilitated.

2-1-1. Step A-1

In this synthesis process A, the 2-amino-quinoxaline-3-carboxyamide compound of the general formula (II), which is a starting material, is caused to react with oxalic monohalide compound of the general formula (III), preferably a monoester monohalide, in the presence of a solvent, preferably in the presence of a base thereby to synthesize an N-(3-carbamoyl-quinoxaline-2-yl)oxamic acid compound, preferably an ester thereof.

Preferable reaction conditions of the step A-1 are as follows.

Preferable reaction conditions of step A-1

Temperature: −40° C. to 100° C., preferably −20° C. to 50° C.
Time: 1 hour to 7 days, preferably 5 hours to 1 day.
Base: ammonia, triethylamine, piperidine, morpholine, pyridine, and other amines, $NaHCO_3$, $Na_2CO_3$, $K_2CO_3$, NaOH, KOH, NaH, and other alkalis.
Solvent: tetrahydrofuran, dioxane, acetone, methylethylketone, chloroform, methylene chloride, dimethylformamide, dimethylacetamide, dimethylsulfoxide, benzene, toluene, higher-boiling solvents which can be used in the subsequent step A-2 which will be explained later in detail, and the like. The quantity of the solvent is 1 to 100 times, preferably 10 to 50 times by weight of that of the compound (II).

Compound (III)/Compound (II) (mole ratio): 0.5 to 5, preferably 1 to 2.

Base/Compound (II) (mole ratio): 0.5 to 5, preferably 1 to 2.

Upon completion of the reaction, an excessive quantity of water is added to the compound (IV), and the object substance can be isolated by filtration in the case where crystals precipitate and by further extraction with an ordinary solvent such as chloroform or ethyl acetate which is immiscible with water and concentration in the case where crystals do not precipitate.

2-1-2. Step A-2

By heating the compound (IV) prepared in this manner in a solvent of high boiling point thereby to dehydrate this compound and cause it to undergo ring closure, a pyrimido [5,6-b] quinoxaline-4(3H)-one-2-carboxylic acid compound, preferably an ester thereof, is obtained.

The preferable reaction conditions of this step A-2 are as follows.

Preferable reaction conditions of step A-2

Temperature: 50° to 400° C., preferably 150° to 300° C.
Time: 5 minutes to 10 hours, preferably 30 minutes to 5 hours.
Solvent: α-chloronaphthalene, diphenylether, "Dowtherm," mineral oil, diethyl oxalate, di-n-butyl oxalate, and the like. The quantity of the solvent is 1 to 100 times, preferably 10 to 50 tims, by weight of that of the compound (IV).
The desired compound (I) can be obtained by transforming the R group of the formed compound (I) or by transformation into a pharmacologically acceptable salt thereof.

2-1-3. Step A-0

The compound (II) can be prepared by any suitable process. Specifically, for example, the process set forth in J. Chem. Soc., 1945, 622 by J. Am. Chem. Soc. 66, 1957-(1941) may be used.

In this connection, with the exception of a few di- and tetra- substituted products, a mixture of two kinds of isomers is obtained when the compound (II) is synthesized by the processes disclosed in these references. If, in this case, the separation of the isomer mixture is difficult, it can be used as it is as the starting material, in which case, a mixture of two kinds of isomers of the compound (I) will be formed.

Substituted products from which the compound (II) can be obtained as a single substance are as follows.

(1) 6,7-di-substituted products $R^1 = R^4 = H, R^2 = R^3 = [A]$ (2) 5,8-di-dubstituted products $R^2 = R^3 = H, R^1 = R^4 = [A]$ (3) 5,6,7,8-tetra-substituted product $R^1 = R^2 = R^3 = R^4 = [A]$ Specific examples of the compound (II) correspond to those set forth as examples with respect to the aforedescribed compound (I) except that the representation of the positions of the groups $R^1$ through $R^4$ are not 6 through 9 - positions as in compound (I) but are 5 through 8-positions in compound (II).

2-2. Synthesis process B

Another preferred process for synthesizing the compound (I) comprises the following steps.

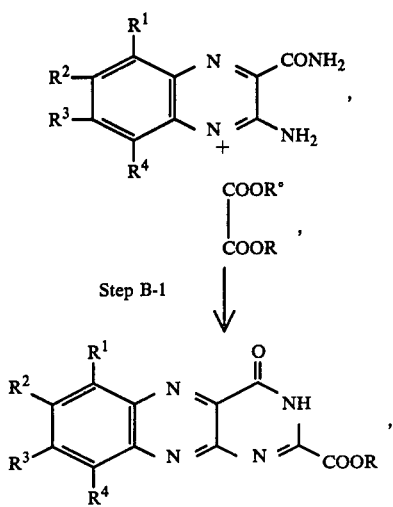

(R, R' through $R^4$ and $R^6$ have the same respective meanings as set forth hereinbefore.)

In this synthesis process B, the 2-aminoquinoxaline-3-carboxyamide compound represented by the formula (II) is caused to undergo reaction under heating with the oxalic compound of the formula (VI), preferably an oxalic diester, whereupon ring closure takes place, and the compound (I) is obtained in the form of an ester. The intermediate prior to ring closure may be synthesized first and then heated to cause it to undergo ring closure as in the case of the aforedescribed synthesis process A, but this is not necessary. The instant reaction is carried out in a solventless mode although the starting material compound (VI) may be said to function as a solvent or in a solvent of high boiling point.

The preferable reaction conditions of this step B-1 are as follows.

Preferable reaction conditions of step B-1

Temperature: 50° to 400° C., preferably 150° to 300° C.
Times: 30 minutes to 3 days, preferably 5 hours to 1 day.
Solvent: α-chloronaphthalene, diphenylether, "Dowtherm," mineral oil, diethyl oxalate, di-n-butyl oxalate, and the like. The solvent quantity is from 1 to 100 times, preferably 5 to 20 times (by weight) that of the compound (II).

Compound (IV)/Compound (II) (mole ratio): 1 to 100, preferably 2 to 50.

Upon completion of this reaction, the compound (I) is isolated through precipitation by adding a solvent of low dissolving power such as n-hexane or petroleum benzene to the reaction liquor.

2-3. Transformation of compound (I)

In the above described synthesis processes A and B, the oxalic compounds (III) and (VI) are preferably esters (R $\neq$ H), in which case, therefore, the resultant compound (I) is also obtained as an ester.

In the case where a compound (I) of a form other than an ester is required for reasons such as pharmacological effectiveness, the ester compound (I) may be transformed into the other form by an ordinary method.

Preferable reaction conditions in the case of transformation into free carboxylic acid by hydrolysis are as set forth below. In the case where an alkali is used for the hydrolytic agent, an alkali metal salt is formed, and for this reason neutralization is carried out with an acid in order to obtain free carboxylic acid. It will be obvious that this alkali metal salt can be recovered as the object product.

Preferably hydrolysis conditions

Alkali: NaOH, KOH, $K_2CO_3$, $Na_2CO_3$, NaH, etc.
Acid: Hydrochloric acid, sulfuric acid, hydrobromic acid, p-toluenesulfonic acid, acetic acid, etc.
Temperature: 0° to 200° C., preferably 20° to 100° C.
Time: 30 minutes to 3 days, preferably 1 hour to 1 day.
Solvent: water, water-dioxane, water-an alcohol, benzene, toluene, etc. The quantity of the solvent relative to the compound (I) is 1 to 100 times, preferably 2 to 50 times (by weight).

3. Allergic asthma medicine

While the compund (I) and salts thereof can be applied to various uses, one important use thereof is that as an allergic asthma medicine.

As an allergic asthma medicine, the compound is inhaled into the bronchi in a dose of 1 to 20 mg., 3 or 4 times daily, in the case of administration by inhalation. In the case of intravenous injection, it it injected in a dose of 1 to 10 mg., 4 or 5 times daily. In the case of oral administration, it is administered in a dose of 1 to 50 mg., 3 times daily, and in the case of rectal administration, it is administered in a dose of 1 to 50 mg., 2 or 3 times daily.

The medicine may be used in any suitable form, but ordinarily, it is used in the form of a composition containing the compound (I), one or more of its salts, an ordinary pharmaceutical carrier, a vehicle, other additives and/or adjuvants.

4. Experimental Examples

I. Tests of medicinal effect

Evaluation of the antiallergic action of the compounds of this invention was carried out by passive cutaneous anaphylaxis (PCA) test on rats.

Egg albumen which has been recrystallized five times and Bodetalla pertussis vaccine were intracutaneously administered into rats (DLC Wister rats), and after 13 days serum was extracted therefrom. The serum thus obtained contained an antibody having characteristics similar to those of human reagin and exhibited an antibody value higher than 256.

This serum was diluted 128 times and intracutaneously administered into the backs of rats, and 48 hours thereafter, suspensions prepared by suspending compounds of this invention in the quantities set forth in Table 1 in respective 1-percent tragacanth solutions were orally administered to respective rats. After 20 minutes, a physiological salt solution in which egg albumen and coloring matter (Evans Blue) had been dissolved was intravenously administered into each rat, 30 minutes thereafter the dorsal skin of the rat was peeled off, and the quantity of the coloring matter which had exuded out as a result of antigen antibody reaction was extracted by means of $Na_2SO_4$ and acetone and subjected to colorimetry at $620\mu$. The results were as indicated in Table 1.

(a) Synthesis of ethyl N(3-carbamoyl-quinoxaline-2-yl)oxamate, the compound (IV) wherein $R^1 = R^2 = R^3 = R^4 = H$, R = ethyl, X = Cl Step A-1).

758 mg. of triethylamine and 940 mg. of 2-aminoquinoxaline-3-carboxyamide are added to 10 ml. of dimethyl formamide. The resulting mixture was cooled to 0° C., and 1.02 g. of ethyl oxalylchloride is added thereto. The resulting materials are agitated at 0° C. for 2 hours and thereafter agitated overnight at room temperature. The resulting materials are added to 75 ml. of water, and the crystals thus precipitated are separated by filtration and then dried. These crystals are then recrystallized from chloroform-n-hexane.

As a result, in one actual practice, 800 mg. (56 percent yield) of yellow crystals of the following properties were obtained.

m.p. 207° to 208° C.

IR 3,430 cm$^{-1}$ (N = H of amide) 1,735 cm$^{-1}$ (C =

TABLE 1

| COMPOUND NO. | COMPOUND | DOSE (mg/Kg) | INHIBITION RATE % |
|---|---|---|---|
| 1 | Ethyl-7,8-dimethoxy-pyrimido [5,6-b]quinoxaline-4 (3H)-one-2-carboxylate | 10<br>1 | 70<br>46 |
| 2 | Ethyl-pyrimido[5,6-b]quinoxaline-4(3H)-one-2-carboxylate | 10<br>1 | 58<br>22 |
| 3 | Ethyl-7,8-dimethyl-pyrimido [5,6-b]quinoxaline-4 (3H) one-2-carboxylate | 50 | 85 |
| 4 | Ethyl-7,8-dichloro-pyrimido[5,6-b]quinoxaline-4 (3H) one-2-carbixylate | | |
| 5 | Butyl-7,8-dimethoxy-pyrimido[5,6-b]quinoxaline-4(3H)-one -2-carboxylate | 50 | 69 |
| 6 | pyrimido[5,6-b]quinoxaline-4 (3H) -one-2-carboxylic acid | 50 | 14 |
| 7 | Isopropyl-7,8-dimethoxy pyrimido[5,6-b]quinoxaline-4(3H)-one-2-carboxylate | 30 | 30 |
| 8 | Benzyl-7,8-dimethoxy-pyrimido[5,6-b]quinoxaline-4(3H)-one-2-carboxylate | 30 | 45 |
| | Ethyl-7-methyl-pyrimido[5,6-b]quinoxaline-4(3H)-one-2-carboxylate | 30 | 97 |
| 9* | Ethyl-8-methyl-pyrimido[5,6-b]quinoxaline-4(3H)-one-2-carboxylate | | |
| | Ethyl-6-methyl-pyrimido[5,6-b]quinoxaline-4(3H)-one-2-carboxylate | 30 | 62 |
| 10* | ethyl-9-methyl-pyrimido[5,6-b]quinoxaline-4(3H)-one-2-carboxylate | | |
| 11 | Ethyl-7,8-di-n-butoxy-pyrimido[5,6-b]quinoxaline-4(3H)-one-2-carboxylate | 30 | 68 |
| 12 | Ethyl-7,8-diethyl-pyrimido[5,6-b]quinoxaline-4(3H)-one-2-carboxylate | 30 | 86 |
| 13 | Ethyl-6,9-dimethoxy-pyrimido[5,6-b]quinoxaline-4(3H)-one--2-carboxylate | 30 | 23 |
| 14 | Ethyl-7,8-methylenedioxy-pyrimido[5,6-b]quinoxaline-4(3H)-one-2-carboxylate | 30 | 91 |
| 15 | Ethyl-6,7,8,9-tetramethyl-pyrimido[5,6-b]quinoxaline-4(3H)-one-2-carboxylate | 30 | 22 |

*Compounds 9 and 10 are mixtures respectively of 7-methyl and 8-methyl derivatives and 6-methyl and 9-methyl derivatives.

II. Safety of the compound of this invention

The compounds 1, 2, 3, 9, 12 and 14 set forth in Table 1 are believed to have the highest effectiveness among the present compounds; the compound 1, for example, was orally administered in a dose of 3,000 mg./Kg. to mice, but there were no cases of death, and no variations in general physiological state were observed.

The degree of safety of the compounds of this invention is considered to be high, LD 50 being more than 3,000.

III. Examples of synthesis (1) Synthesis of ethyl-pyrimido [5,6-b] quinoxaline-4(3H)-one-2-carboxylate, the compound (I) wherein $R^1 = R^2 = R^3 = R^4 = H$. R = ethyl.
PROCESS A:

(b) Synthesis of ethyl pyrimido [5,6-b] quinoxaline-4(3H)-one-2-carboxylate (Step. A-2)

720 mg. of ethyl N (3-carbamoyl-quinoxaline-2-yl) oxamate is dissolved in 20 ml. of α-chloronaphthalene, and the resulting solution is heated at a temperature of 220° C. to 230° C. for 4 hours as the water formed is removed. After cooling, an excessive quantity of n-hexane is added, and the crystals thus precipitated are collected by filtration. These crystals are then dissolved in chloroform and treated with activated carbon. Thereafter, the solute is recrystallized from chloroform-n-hexane.

As a result, in one actual practice, 510 mg. (76 percent yield) of yellow crystals of the following properties were obtained.

m.p. 237.5° to 240° C.

IR 3,200 to 2,900 cm$^{-1}$ 1,705 cm$^{-1}$ (C = O of ester)

O of ester) 1,690 cm$^{-1}$ (C = O of amide)

1,695 cm$^{-1}$ (C = O of 4-position)
1,295 to 1,260 cm$^{-1}$ (C = O of ester)
M.S. m/e (%) 270 (24) M$^+$, 198 (94), 170(100), 143 (31)

Similarly as described above, the compounds set forth in the following Tables 2(1), 2(2), and 2(3) were synthesized.

These crystals are dissolved in chloroform, and n-hexane is added thereto until a small quantity of crystals begins to appear. The process materials are treated with activated carbon, and then n-hexane is added thereto in excessive quantity. The crystals thus precipitating are collected by filtration.

As a result, in one actual practice, 85 mg. (31 percent

Table 2 (1)

| COMPOUND NAME | MELTING POINT | IR | M.S. m/e (%) |
|---|---|---|---|
| Ethyl-7,8-dimethoxy-pyrimido[5,6-b]quinoxaline-4(3H)-one-2-carboxylate | 234~ 238° C | 3,100~ 2,800 cm$^{-1}$<br>1,700cm$^{-1}$ 1,500cm$^{-1}$<br>1,300cm$^{-1}$ 1,230cm$^{-1}$ | 330(54)M$^{30}$<br>258(100) |
| Ethyl-7,8-dimethyl-pyrimido[5,6-b]quinoxaline-4(3H)-one-2-carboxylate | 235°C (decomposed) | 3,200~ 2,800c,$^{-1}$<br>1,700 cm$^{-1}$ 1,360cm$^{-1}$<br>1,300cm$^{-1}$ | 298(32)M$^+$<br>226(100)<br>198 (66) |
| Ethyl-7,8-dichloro-pyrimido [5,6-b]-quinoxaline-4(3H)-one-2-carboxylate | 240~ 250° C | 3,200~ 2,800cm$^{-1}$<br>1,705cm$^{-1}$ 1,695 cm$^{-1}$<br>1,300~ 1,280cm$^{-1}$ | 340 (19) M$^+$<br>338 (27)M$^+$<br>268 (67)<br>266(100)<br>240 (54)<br>238 (77) |
| *Ethyl-7-methyl-pyrimido[5,6-b]quinoxaline-4-(3H)-one-2-carbixylate | 218~ 230° C (decomposed) | 3,600~ 3,300 cm$^{-1}$<br>3,200~ 2,850 cm$^{-1}$ | 284 (41)M$^+$<br>212(100) |
| *Ethyl-8-methyl-pyrimido- [5,6-b]-quinoxaline-4(3H)-one-2 carboxylate | | 1700 cm$^{-1}$<br>1,310 ~ 1,250 cm$^{-1}$ | 184(67) |
| **Ethyl-6-methyl-pyrimido [5,6-b]quinoxaline-4(3H)-one-2-carboxylate | 215°~ 226° C (decomposed) | 3,480 cm$^{-1}$<br>3,290 ~ 2,900cm$^{-1}$<br>1,700 cm$^{-1}$ 1,540cm$^{-1}$ | 284 (41) M$^+$<br>212(100) |
| **Ethyl-9-methyl-pyrimido-[5,6-b]-quinoxaline-4(3H)one-2-carboxylate | | 1320~ 1,240cm$^{-1}$ | 184(58) |
| Ethyl-7,8-di-n-butoxy-pyrimido [5,6-b]-quinoxaline-4(3H) one-2-carboxylate | 212~ 215° C | 3,620~ 3,300cm$^{-1}$<br>3,000~ 2,800cm$^{-1}$<br>1,695cm$^{-1}$<br>1,500~ 1,420cm$^{-1}$<br>1,300cm$^{-1}$ 1,200cm$^{-1}$ | 414 (44) M$^+$<br>287 (39)<br>230 (100) |
| Ethyl-7,8-diethyl-pyrimido[5,6-b]-quinoxaline-4(3H)one-2-carboxylate | 204~ 212° C | 3,620 ~ 3,300cm$^{-1}$<br>3,020~ 2,900cm$^{-1}$<br>1700cm$^{-1}$ 1,460cm$^{-1}$<br>1,300 cm$^{-1}$ | 326 (30) M$^+$<br>254 (100)<br>211 (31) |
| Ethyl-6,9-dimethoxy-pyrimido [5,6-b]quinoxaline-4(3H)-one-2-carboxylate | 205~ 211° C | 3,600~ 2,800cm$^{-1}$<br>1,740~ 1,650cm$^{-1}$<br>1,640~ 1,560cm$^{-1}$<br>1,260cm$^{-1}$ | 330 (11) M$^+$<br>243 (100)<br>233 (60)<br>188 (25) |
| Ethyl-7,8-methylenedioxy-pyrimido [5,6-b]-quinoxaline-4(3H)-one-2-carboxylate | 234~ 240° C (decomposed) | 3,640~ 3,300 cm$^{-1}$<br>1,695cm$^{-1}$ 1,460cm$^{-1}$<br>1,300cm$^{-1}$ 1,225cm$^{-1}$<br>1,020cm$^{-1}$ | 314 (26) M$^+$<br>242 (64)<br>214 (57)<br>18 (100) |
| Ethyl-6,7,8,9-tetramethyl-pyrimido [5,6-b]-quinoxaline-4(3H)-one-2-carboxylate | 232~ 236° C (decomposed) | 3,650~ 2,800cm$^{-1}$<br>1,750~ 1,640cm$^{-1}$<br>1,320~ 1,240cm$^{-1}$ | 326 (100) M$^+$<br>271 (22)<br>254 (69)<br>226 (30) |

*A mixture of 7-methyl and 8-methyl derivatives
**A mixture of 6-methyl and 9-methyl derivatives.

Process B:

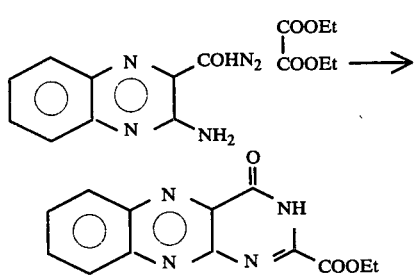

188 mg. of 2-amino-quinoxaline-3-carboxyamide, the compound (II) wherein R$^1$ = R$^2$ = R$^3$ = R$^4$ = H, is dissolved in 5 ml. of diethyl oxalate, the compound (VI) wherein R = R$^0$ = ethyl, and the resulting solution is refluxed for 24 hours as water and by-product ethanol are removed. 10 ml. of n-hexane is added to the resulting materials, and insoluble substances are removed by filtration. An excessive quantity of n-hexane is added to the filtrate, and the crystals thus precipitated are collected by filtration.

yield) of yellow crystals were obtained. The melting point, IR, and M.S. of these crystals are respectively same as those of the crystals obtained by process A.

(2) Synthesis of butyl-7,8-dimethoxypyrimido[5,6-b]quinoxaline-4(3H)-one-2-carboxylate, the compound (I), wherein R$^1$ = R$^4$ = H, R$^2$ = R$^3$ = methoxy, R = butyl Process A:

(a) 496 mg. of 2-amino-6,7-dimethoxy-quinoxaline-3-carboxylate, the compound (II), wherein R$^1$ = R$^4$ = H, R$^2$ = R$^3$ = methoxy, is dissolved in 4 ml. of dimethylformamide. To the resulting solution, as it is agitated at 0° C., 410 mg. of butyl oxalylchloride, the compound (III), wherein X = Cl, R = butyl, and 330 mg. of triethylamine are gradually added. After agitation for 1 hour at 0° C., the resulting materials are left standing overnight at room temperature.

The materials are then added into 30 ml. of water, and the crystals thus precipitating out are collected by filtration and recrystallized from chloroform-n-hexane.

As a result, 334 mg. (44 percent yield) of crystals are obtained.

(b) The crystals thus obtained are dissolved in 20 ml. of α-chloronaphthalene, and the resulting solution is heated at 230° C. to 240° C. for 3 hours. After cooling, n-hexane in excessive quantity is added to the solution, and the crystals thus precipitating out are collected by filtration. These crystals are recrystallized from chloroform-n-hexane.

As a result, 280 mg. (88 percent yield) of yellow crystals having the following properties are obtained.
m.p. above 230° C.
IR 3,100 to 2,800 cm$^{-1}$ 1,705 cm$^{-1}$, 1,495 cm$^{-1}$, 1,300 cm$^{-1}$, 1,230 cm$^{-1}$
M.S. m/e (%) 358 (46)M$^+$, 275 (42), 258 (100), 230 (46)

(3) Synthesis of isopropyl-7,8-dimethoxypyrimido[5,6-b]quinoxaline-4(3)-one-2-carboxylate, the compound (I) wherein $R^1 = R^4 = H$, $R^2 = R^3 =$ methoxy, R = isopropyl Process A:

(a) 1.24 g. of 2-amino-6,7-dimethoxy-quinoxaline-3-carboxyamide, the compound (II) wherein $R^1 = R^4 = H$, $R^2 = R^3 =$ methoxy, and 606 mg. of triethylamine are dissolved in 20 ml. of dimethylformamide. As the reaction liquor is maintained at 0° C. and agitated, 903 mg. of isopropyl oxalylchloride, the compound (III) wherein X = Cl, R = issopropyl was added thereto by dropping. The resulting reaction liquor is agitated at 0° C. for 2 hours and then left standing overnight at room temperature. The entire liquor is added into 100 ml. of ice water, and the crystals thus precipitating out are collected by filtration and dried.

As a result, 1.52 g. (84 percent yield) of light yellow crystals were obtained.

(b) The crystals thus obtained are dissolve in 30 ml. of α-chloronaphthalene, and the resulting solution is heated at 225° C. to 235° C. for 3 hours. After cooling, the crystals precipitating out are collected by filtration. These crystals are recrystallized from chloroform-n-hexane.

As a result, 880 mg. (61 percent yield) of yellow crystals having the following properties were obtained.
m.p. higher than 250° C. (decomposes)
IR 3,600 to 3,300 cm$^{-1}$ 1,710 cm$^{-1}$, 1,600 cm$^{-1}$. 1,490 cm$^{-1}$, 1,230 cm$^{-1}$
M.S. m/e (%) 344 (1) M$^+$, 258 (100), 215 (21)

(4) Synthesis of benzyl-7,8-dimethoxypyrimido[5,6-b]quinoxaline-4(3H)-one-2-carboxylate, the compound (I) wherein $R^1 = R^4 = H$, $R^2 = R^3 =$ methoxy, R = benzyl Process A:

(a) 2.48 g. of 2-amino-6,7-dimethoxy-quinoxaline-3-carboxyamide, the compound (II) wherein $R^1 = R^4 = H$, $R^2 = R^3 =$ methoxy, and 1.31 g. of triethylamine are dissolved in 40 ml. of dimethylformamide. As the reaction liquor is maintained at 0° C. with agitation, 2.58 g. of benzyl oxalylchloride is added thereto by dropping. The reaction liquor is then agitated at 0° C. for 2 hours, after which it is left standing overnight at room temperature. The entire quantity of this reaction liquor is added into 200 ml. of ice water, and the crystals precipitating out are collected by filtration and dried.

As a result, 2.75 g. (68 percent yield) of yellow crystals are obtained.

(b) The crystals thus obtained are dissolved in 80 ml. of chloronaphthalene, and the resulting solution is heated at 220° C. to 230° C. for 4 hours. After cooling, the crystals precipitating out are collected by filtration and then recrystallized from chloroform-n-hexane.

As a result, 1.33 g. (51 percent yield) of yellow crystals having the following properties are obtained.
m.p. 225° to 235° C. (decomposed)
I.R. 3,640 to 3,200 cm$^{-1}$ 1,705 cm$^{-1}$, 1,500 cm$^{-1}$, 1,235 cm$^{-1}$.
M.S. m/e (%) 392 (6) M$^+$, 348 (30) 258 (100), 91(62)

(5) Synthesis of pyrimido[5,6-b]quinoxaline-4(3H)-one-2-carboxylic acid, the compound (I) wherein $R^1 = R^2 = R = H$

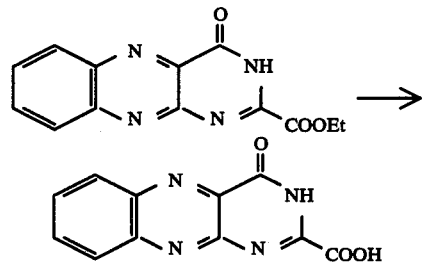

To 405 mg. of ethyl-pyrimido[5,6-b]quinoxaline-4(3H)-one-2-carboxylate, the compound (I) wherein $R^1 = R^2 = R^3 = R^4 = H$, R = ethyl, 18 ml. of a 15-percent solution of NaOH was added, and the reaction liquor is agitated overnight at room temperature. The crystals which precipitated out are collected by filtration and dissolved in 20 ml. of water. After removal of insoluble matter by filtration, the filtrate is adjusted to pH2 with 10-percent HCl, and the solution was concentrated to approximately 10 ml. The crystals precipitating out are collected by filtration.

As a result, 320 mg. (88 percent yield) of yellow crystals having the following propertkes were obtained.
m.p. higher than 250° C.
IR 3,380 cm$^{-1}$, 1,700 cm$^{-1}$
M.S. m/e (%) 198 (100) M$^+$ - 44, 70(42), 145 (37), 143 (70), 118 (36).

What we claim is:

1. A Substituted pyrimido[5,6-b]quinoxaline-4(3H)-one-2-carboxylic acid compound represented by the formula

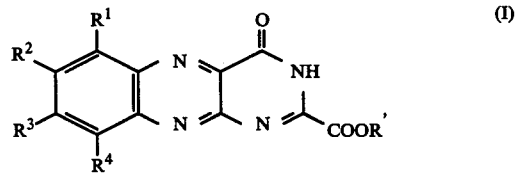

wherein: R designates a member selected from the group consisting of hydrogen, alkyl groups having 1 to 4 carbon atoms, benzyl group, and phenyl group; and each of $R^1$, $R^2$, $R^3$, and $R^4$ independently designates a member selected from the group consisting of hydrogen, alkyl groups having 1 to 4 carbon atoms, alkoxy groups having 1 to 4 carbon atoms, halogens, benzyloxy group, hydroxy group, alkylthio groups having 1 to 4 carbon atoms, and alkylenedioxy groups having 1 to 4 carbon atoms and formed by the bonding of two of $R^1$, $R^2$, $R^3$, and $R^4$, or a pharmacologically acceptable salt of said compound.

2. The compound as claimed in claim 1 in which said substituted pyrimido[5,6-b]quinoxaline-4(3H)-one-2-carboxilic acid compound is a member selected from the group consisting of:

ethyl-pyrimido[5,6-b]quinoxaline-4(3H)-one-2-carboxylate,
ethyl-7,8-dimethoxy-pyrimido[5,6-b]quinoxaline-4(3H)-one-2-carboxylate,
ethyl-7,8-dimethyl-pyrimido[5,6-b]quinoxaline-4(3H)-one-2-carboxylate,
ethyl-7,8-dichloro-pyrimido[5,6-b]quinoxaline-4(3H)-one-2-carboxylate,
ethyl-7-methyl-pyrimido[5,6-b]quinoxaline-4(3H)-one-2-carboxylate,
ethyl-8-pyrimido[5,6-b]quinoxaline-4(3H)-one-2-carboxylate,
ethyl-6-methyl-pyrimido[5,6-b]quinoxaline-4(3H)-one-2-carboxylate,
ethyl-9-pyrimido[5,6-b]quinoxaline-4(3H)-one-2-carboxylate,
ethyl-7,8-di-n-butoxy-pyrimido[5,6-b]quinoxaline-4(3H)-one-2-carboxylate,
ethyl-7,8-diethyl-pyrimido[5,6-b]quinoxaline-4(3H)-one-2-carboxylate,
ethyl-6,9-dimethoxy-pyrimido[5,6-b]quinoxaline-4(3H)-one-2-carboxylate,
ethyl-7,8-methylenedioxy-pyrimido[5,6-b]quinoxaline-4(3H)-one-2-carboxylate,
butyl-7,8-dimethoxy-pyrimido[5,6-b]quinoxaline-4(3H)-one-2-carboxylate,
isopropyl-7,8-dimethoxy-pyrimido[5,6-b]quinoxaline-4(3H)-one-2-carboxylate,
benzyl-7,8-dimethoxy-pyrimido[5,6-b]quinoxaline-4(3H)-one-2-carboxylate,
pyrimido[5,6-b]quinoxaline-4(3H)-one-2-carboxylic acid, and
ethyl-6,7,8,9-tetramethyl-pyrimido[5,6-b]quinoxaline-4(3H)-one-2-carboxylate.

3. A medicinal composition useful in the treatment of allergic asthma which comprises
a pharmacologically active amount of a substituted pyrimido[5,6-b]quinoxaline-4(3H)-one-2-carboxylic acid compound or a pharmacologically acceptable salt thereof, said compound being represented by the formula

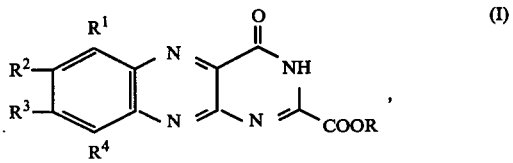

wherein: R designates a member selected from the group consisting of hydrogen, alkyl groups having 1 to 4 carbon atoms, benzyl group, and phenyl group; and each of $R^1$, $R^2$, $R^3$ and $R^4$ independently designates a member selected from the group consisting of hydrogen, alkyl groups having 1 to 4 carbon atoms, alkoxyl groups having 1 to 4 carbon atoms, halogens, benzyloxy group, hydroxyl group, alkylthio groups having 1 to 4 carbon atoms, and alkylenedioxy groups having 1 to 4 carbon atoms and formed by the bonding of two of $R^1$, $R^2$, $R^3$ and $R^4$, or pharmacologically acceptable salts of said compounds; and
a pharmaceutical carrier.

4. The medicinal composition of claim 3 in which said substituted pyrimido[5,6-b]quinoxaline-4(3H)-one-2-carboxylic acid compound is a member selected from the group consisting of:

ethyl-pyrimido[5,6-b]quinoxaline-4(3H)-one-2-carboxylate,
ethyl-7,8-dimethoxy-pyrimido[5,6-b]quinoxaline-4(3H)-one-2-carboxylate,
ethyl-7,8-dimethyl-pyrimido[5,6-b]quinoxaline-4(3H)-one-2-carboxylate,
ethyl-7,8-dichloro-pyrimido[5,6-b]quinoxaline-4(3H)-one-2-carboxylate,
ethyl-7-pyrimido[5,6-b]quinoxaline-4(3H)-one-2-carboxylate,
ethyl-8-methyl-pyrimido[5,6-b]quinoxaline-4(3H)-one-2-carboxylate,
ethyl-6-methyl-pyrimido[5,6-b]quinoxaline-4(3H)-one-2-carboxylate,
ethyl-9-methyl-pyrimido[5,6-b]quinoxaline-4(3H)-one-2-carboxylate,
ethyl-7,8-di-n-butoxy-pyrimido[5,6-b]quinoxaline-4(3H)-one-2-carboxylate,
ethyl-7,8-diethyl-pyrimido[5,6-b]quinoxaline-4(3H)-one-2-carboxylate,
ethyl-6,9-diemthoxy-pyrimido[5,6-b]quinoxaline-4(3H)-one-2-carboxylate,
ethyl-7,8-methylenedioxy-pyrimido[5,6-b]quinoxaline-4(3H)-one-2-carboxylate,
butyl-7,8-dimethoxy-pyrimido[5,6-b]quinoxaline-4(3H)-one-2-carboxylate,
isopropyl-7,8-dimethoxy-pyrimido[5,6-b]quinoxaline-4(3H)-one-2-carboxylate,
benzyl-7,8-dimethoxy-pyrimdo[5,6-b]quinoxaline-4(3H)-one-2-carboxylate,
pyrimido[5,6-b]quinoxaline-4(3H)-one-2-carboxylic acid, and ethyl-6,7,8,9-tetramethyl-pyrimido[5,6-b]quinoxaline-4(3H)-one-2-carboxylate.

* * * * *